United States Patent [19]

Englehart et al.

[11] Patent Number: 4,917,096

[45] Date of Patent: Apr. 17, 1990

[54] PORTABLE ULTRASONIC PROBE

[75] Inventors: Theodore M. Englehart; Richard F. Morris; Narendra T. Sanghvi, all of Indianapolis, Ind.

[73] Assignee: Laboratory Equipment, Corp., Mooresville, Ind.

[21] Appl. No.: 125,403

[22] Filed: Nov. 25, 1987

[51] Int. Cl.$^4$ ............................................. A61B 8/00
[52] U.S. Cl. ................................. 128/660.1; 73/633
[58] Field of Search ................................. 73/618–623, 73/625, 633, 640, 641; 128/600.08–660.10

[56] References Cited

U.S. PATENT DOCUMENTS

| | | | |
|---|---|---|---|
| 3,480,002 | 11/1969 | Flaherty et al. | 128/660.09 |
| 3,845,463 | 10/1974 | Timbs | 73/633 |
| 3,856,985 | 12/1974 | Yokoi et al. | 73/620 X |
| 4,084,582 | 4/1978 | Nigam | 128/660.1 |
| 4,186,747 | 2/1980 | Iinuma | 128/660.08 |
| 4,238,962 | 12/1980 | Toemzer | 73/633 |
| 4,257,272 | 3/1981 | Sloman | 73/633 |
| 4,294,119 | 10/1981 | Soldner | 73/625 |
| 4,455,872 | 6/1984 | Kossoff et al. | 73/633 X |
| 4,478,083 | 10/1984 | Hassler et al. | 73/620 |
| 4,637,256 | 1/1987 | Sagiyama et al. | 73/633 |

*Primary Examiner*—Francis Jaworski
*Attorney, Agent, or Firm*—Woodard, Emhardt, Naughton Moriarty & McNett

[57] ABSTRACT

A hand-held portable ultrasonic scanning probe for use with energizing and receiving means for imaging sections of a body includes a fluid-filled enclosure coupled to a handle portion which houses a DC drive motor. The output shaft of the drive motor is directly coupled to a level wind drive screw. A holder assembly incorporating a pawl which coacts with the drive screw and a plano-concave transducer moves back and forth across the drive screw as a result of the DC motor output shaft rotation. The linear travel of the transducer creates a linear scan thereby eliminating the diagnostic imaging problems of sector scans.

12 Claims, 4 Drawing Sheets

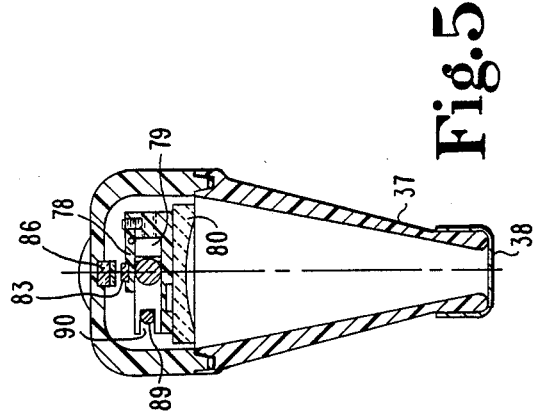
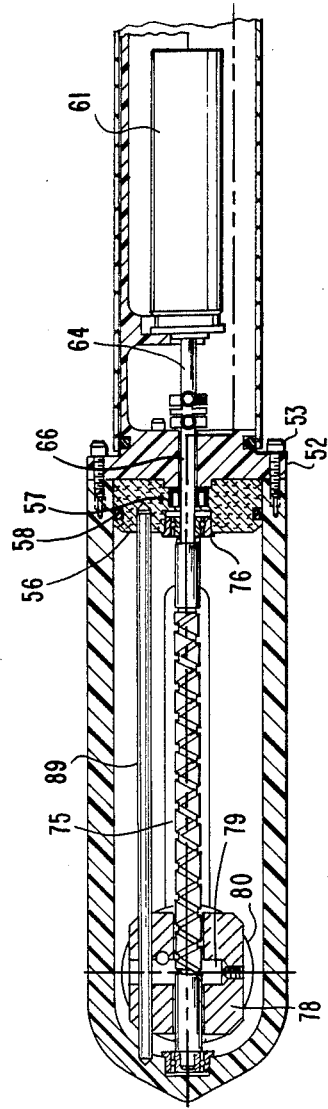
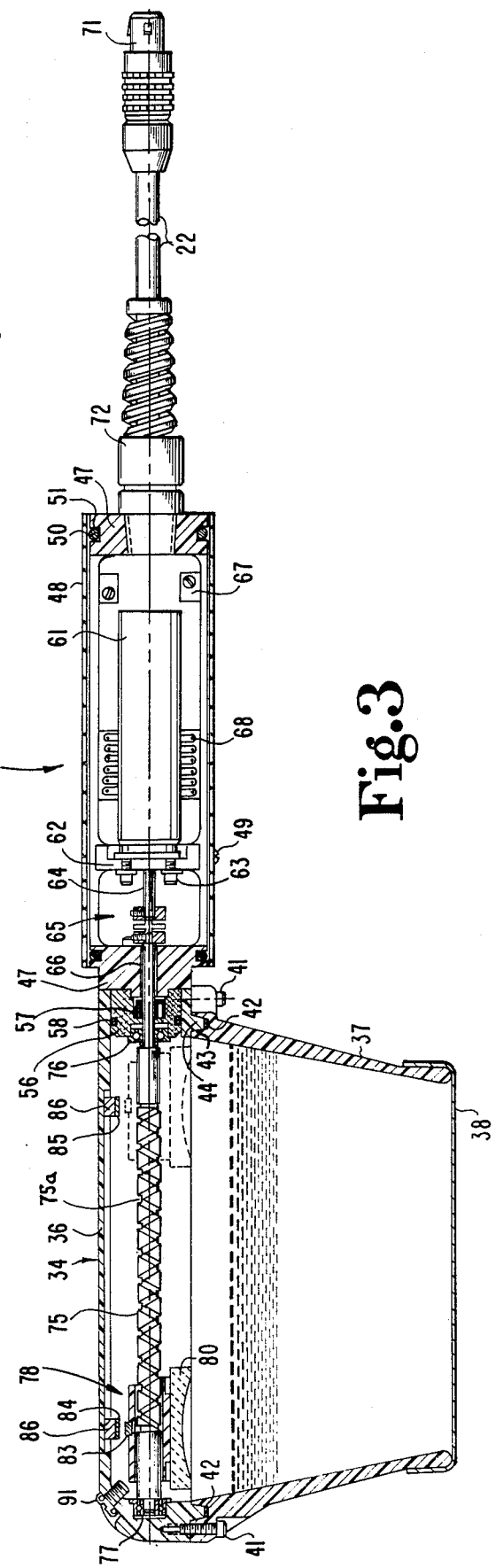

PORTABLE ULTRASONIC PROBE

BACKGROUND OF THE INVENTION

The present invention relates in general to medical imaging devices and techniques which use ultrasound. More particularly, the present invention pertains to hand-held, portable imaging probes and the structure of such probes which enable the automatic scanning of the transmitted ultrasound beam.

Medical imaging by the use of ultrasound had become a fairly well-known technique in the late 1960's and early 1970's. Early uses of ultrasonic techniques involved clinical diagnosis in the fields of obstetrics, urology and cardiology. More recently such techniques have become increasingly important in visualization of other body portions such as vascular applications and the scanning of breasts to detect tumors. Ultrasonic diagnostics has been shown to be capable of revealing, noninvasively, in pictorial fashion, tomographic cross sections of most internal human organs. In a number of cases, the use of ultrasound has made possible the diagnosis of disease (or the absence of), for example, cysts, tumors, or cancer in organs, in situations where other diagnostic methods such as radiography by themselves were found to be either inapplicable, insufficient, or unduly hazardous.

In those devices which utilize the pulse-echo method, pulses of ultrasonic energy are generated by a transducer, which has been properly energized by separate electrical circuitry. This ultrasonic energy generated by the transducer is focused and directed into the portion of the body to be imaged. When this focused beam (series of pulses) reaches an interface between two different materials or types of tissue, some of the transmitted ultrasound is reflected due to a characteristic impedance mismatch at the interface. In those devices employing a single transducer, it must operate in both the pulse and receive modes. In such an arrangement, after a pulse is transmitted, the transducer is placed in a receive mode in order to receive any reflected ultrasound and convert those received echoes into image-representative electrical signals. The time of arrival of the echo and its amplitude give information regarding the interface such as its depth into the body and the nature of the tissue. The image-representative electrical signals are able to be displayed in a number of different forms. The most common are referred to as an A-scan, B-scan, C-scan and M-scan. Each of these forms of display are well known and thoroughly described and analyzed in the ultrasound literature. Scan conversion circuitry is employed to receive and process the image-representative electrical signals prior to display in order to enable a diagnostically meaningful display.

A relatively popular form of data display for diagnostic imaging is the B-scan because the information is displayed in a manner similar to a conventional television. Radial or linear B scan is preferred for longitudinal and transverse cross sections. The B scan technique is two dimensional and provides a cross-sectional picture in the plane of the scan. The picture which results can also be recorded either photographically or on recording tape for retention and VCR playback.

Since ultrasonic imaging of the type mentioned is typically used as diagnostic tool, it is advantageous to be able to move the beam of ultrasound around the body so as to investigate different planes or slices. In arrangements with stationary transducers and ultrasound beams, it was found that predictability and uniformity of beam movement were important to the quality and diagnostic value of the resultant images. A result of this perceived importance on the predictability and uniformity of beam movement was to employ certain scanning arrangements whereby the beam of ultrasound could be mechanically or electrically moved in a predetermined and uniform manner. Although the probe which houses the transducer may still be moved manually over different portions of the body, an internal scanning technique which uniformly moves the beam in a precisely timed fashion, regardless of the probe placement on the body, is helpful in order to scan a larger area at each fixed position of the probe.

One such internal scanning technique is disclosed in U.S. Pat. No. 4,084,582 which issued Apr. 18, 1978 to Anant K. Nigam. Disclosed in this reference is a hand-held probe, which is fluid-filled and employs a fixed transducer and focusing lens. The scanning is performed by an oscillating reflector (mirror) which scans the generated beam of ultrasound pulses received from the transducer and reflected out through a flexible membrane covered window. In this particular approach, the scanning or oscillating mirror creates a sector scan and for distances deeper into the body the fanning out of the sector results in geometrical distortion when the image information is then later presented on a generally square or rectangular display. The problem which is encountered is that the density of information varies across the display and results in image information which is not as easily interpreted and may give rise to diagnostic error.

The present invention corrects this sector scan deficiency by the novel approach of using a lightweight focusing transducer which is moved back and forth linearly over the same axis thereby avoiding the sector scan problems. In a related embodiment a plurality of lightweight focusing transducers are used in order to create a real-time scan. A further advantage of the present invention is that it avoids the need for a focusing lens by a novel transducer design which provides the needed pulsing and receiving piezoelectric capabilities in a plano-concave form which as a result is self-focusing. By direct focus of the beam and the elimination of a reflective scanning mirror, concerns over total reflection from the mirror, the critical angle and material selection are obviated.

SUMMARY OF THE INVENTION

A portable ultrasonic scanning probe for use with energizing means and receiving means for imaging sections of the body according to one embodiment of the present invention comprises a fluid-tight enclosure, a fluid contained within said enclosure, transducer means disposed within said enclosure and operable in response to the energizing means to generate an ultrasound beam and drive means for moving the transducer means back and forth on a common axis in a substantially linear path.

One object of the present invention is to provide an improved portable ultrasonic imaging probe providing linear scan by linear movement of the transducer.

Related objects and advantages of the present invention will be apparent from the following description.

BRIEF DESCRIPTION OF THE DRAWINGS

FIG. 3 is a side elevation view in partial section of the FIG. 1 probe.

FIG. 4 is a top plan view in partial section of the FIG. 1 probe.

FIG. 5 is a front elevation view in partial section of the FIG. 1 probe.

DESCRIPTION OF THE PREFERRED EMBODIMENT

Figure 1:
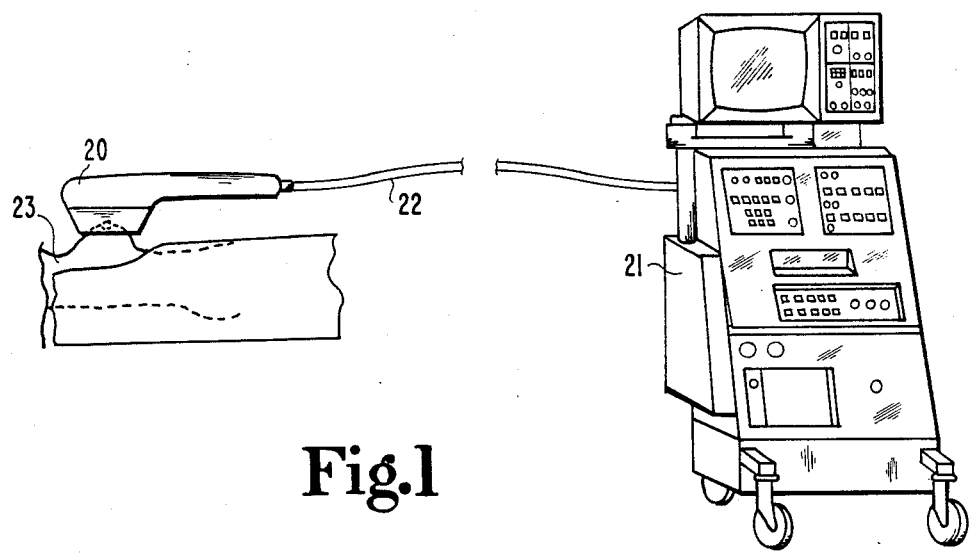
FIG. 1 is a diagrammatic view of a portable ultrasonic scanning probe as arranged with an electrical equipment console and the patient being scanned according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated a hand-held, portable ultrasonic imaging probe 20 which is operably and electrically coupled to console 21 by way of cable 22. In diagrammatic and phantom line form in a representation of the patent 23 prepared by ultrasonic examination. Although the illustrated probe 20 may be used for a variety of anatomical investigations, the illustrated embodiment has as its primary and intended purpose breast examinations. This type of examination, as contrasted to cardiovascular examinations, has specific requirements such as the desired depth of focus into the body, the rate of scan, and the absence of any need for real-time imaging due to the lack of anatomical movement occurring within the particular organ being examined. When real-time imaging is necessary or desired, this can be achieved within the teachings of the present invention by going to multiple elements (FIG. 6) or a single element of a faster rate of travel with suitable counterbalancing (FIG. 7).

Figure 2:
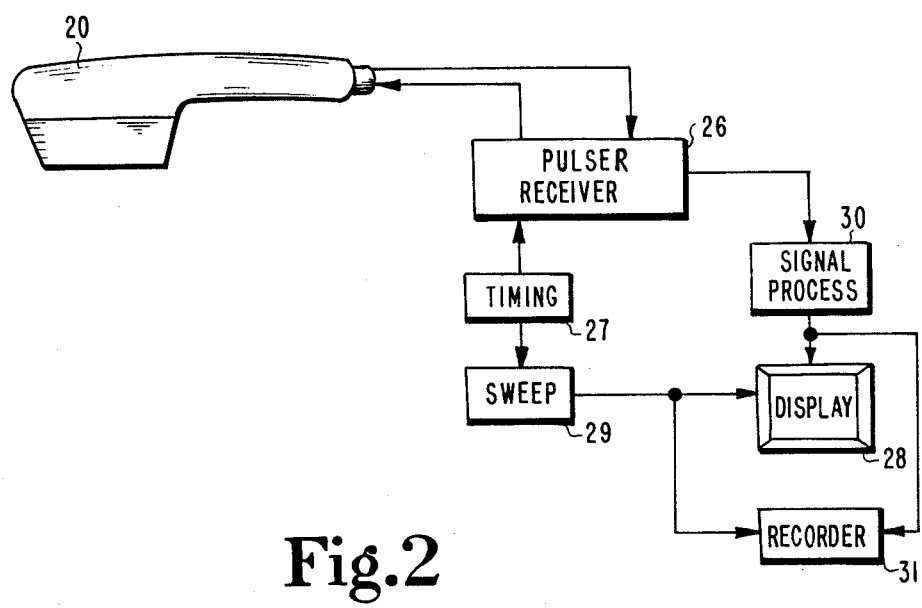
FIG. 2 is a schematic illustration of the FIG. 1 probe in combination with, and in block diagram form, associated electronics.

Referring to FIG. 2, there is illustrated in schematic form the general circuitry blocks and components for use in generating and receiving the necessary pulse-echo signals and for displaying and recording the image-representative information which is received from the transducer. Inasmuch as the focus of the present invention is on the design and structure of probe 20, the details of the support electronics which are well known is not believed to be necessary. Further, no attempt has been made to tabulate every conceivable option and variable that are possible with ultrasonic imaging equipment of this type. For example, in cardiovascular applications, doppler detection may be desirable as might a moving target indicator. These types of features are not included in the FIG. 2 representation.

Speaking in general terms, probe 20 is connected to a suitable pulser-receiver circuit 26. The pulser is the portion which energizes the transducer by sending electrical signals to the piezoelectric transducer which then converts the received electrical signals into an ultrasound wave or series of pulses. As these pulses strike a tissue interface within the body, such as a tumor or cyst, sound echoes return and are received by the same transducer which is switched into in a receive or listen mode. The transducer converts these mechanical echo pulses into electrical signals, the cumulation of which are representative of the interface image. These electrical signals are returned to the pulser-receiver circuit 26.

In order to properly time the transmit and receive modes of operation for the pulser-receiver circuit 26, a timing circuit 27 is required. If the image of the interface, such as a tumor or cyst is going to be displayed as video on monitor 28, then the timing information is used to coordinate the sweep of the monitor display with the pulser-receiver circuit by way of sweep circuit 29. A suitable signal processing circuit 30 is used to prepare the received image-representative electrical signals for display or placement on hard-copy recording such as video or magnetic tape by way of recorder 31. Signal processing circuit 30 includes scan conversion, the required filtering, demodulation and amplification in order to present the image information in a meaningful fashion.

Referring to FIG. 3, probe 20 is illustrated as a side elevation view in full section. Probe 20 includes a fluid-filled enclosure 34 and a handle 35 which houses the motor drive for the automatic scanning movement. Enclosure 34 includes top cover 36, a lower, tapered wall portion 37, and a membrane covering 38 for the ultrasound window which is created by the lower or distal peripheral edge of wall portion 37.

Top cover 36 and wall portion 37 are assembled to one another in a fluid-tight enclosing manner by means of screws 41 which are threadedly received by the top cover. O-ring 42 is compressed into a sealing configuration by the action of channel 43 and cooperating projection 44. Although the entire interior void of enclosure 34 is filled with fluid, the fluid lines have only been added in the lower portion in order to provide greater drawing clarity.

Handle 35 includes a machined housing member 47 which is covered by sleeve 48 which is attached to the housing by screws 49. Each end of housing 57 is fitted with an O-ring 50 disposed in annular channels 51 as a means to seal the interior of housing 47. As is best illustrated in the top section view of FIG. 4, housing 47 is flanged laterally with flange portions 52 which are used as the means of attachment of the housing to the top cover 36 by means of screws 53.

In view of the fact that enclosure 34 is fluid-filled and must be fluid-tight to prevent leakage into the interior of handle 35, the end of top cover 36 which is immediately adjacent housing 47 includes a snugly fitted plug 56, a fluorocarbon shaft seal 57, and an O-ring 58. Fluorocarbon shaft seal 57 is important due to the fact that there is a direct drive between the enclosure and handle by way of a shaft which extends from handle 35 into enclosure 34.

Disposed within housing 47 in a drive motor/encoder 61 which is a DC brush, 6-volt style with a 6.3 to 1 gear head ratio. Motor/encoder 61 is a one-directional, rotary drive motor. Drive motor 61 is rigidly mounted to shelf 62 by means of screws 63 as illustrated. Output shaft 64 of drive motor 61 is secured into one end of flexible coupling 65 and the other end of that coupling is rigidly attached to drive shaft 66. Associated electronics for proper setting and control of drive motor 61 include two 10K ohm, 12-turn potentiometers 67 and 6-pin printed circuit boards 68. As previously indicated, communication between probe 20 and electrical console 21 is established by way of cable 22. This cable is a 9-conductor 26-gauge shielded coax which interfaces with console 21 by way of connector 71 and at the opposite end its attachment to probe 20 includes strain relief connector 72.

Disposed within the fluid-filled portion of enclosure 34 is a level winding drive screw 75 which is supported at each end by a flanged ball bearing ring 76 and 77, respectively. Ball bearing ring 76 is seated within plug 56 and in an aligned fashion ball bearing ring 77 is seated within the end wall portion of top cover 36. Drive shaft 66 is rigidly and axially joined to drive screw 75 and in this regard, drive shaft 66 may be either an integral extension of drive screw 75 or separately machined and attached.

Assembled to drive screw 75 is transducer holder 78 which carries both drive screw pawl 79 and transducer 80. A curved protrusion of pawl 79 accurately and precisely interfaces with the reversing thread pitch channels 75a of drive screw 75. Since drive motor/encoder 61 drives in only one direction, the level winding drive screw is required in order to move transducer 80 back and forth in a substantially linear fashion on the same axis of travel. As drive motor 61 is energized, and its output shaft rotates, this rotational motion is imparted to drive screw 75 by way of coupling 65 and although drive screw otherwise remains stationary within its bearing mounts, its rotary action cooperates with pawl 79 causing the pawl to travel up and down the drive screw which in turn moves the holder and transducer which are cooperatively assembled as a single unit.

Disposed in the upper surface of transducer holder 78 is a magnet 83 whose alignment and positioning is important relative to the travel along lead screw 75 and the placement of Hall effect sensors 84 and 85. Sensors 84 and 85 are suspended from the interior surface of top cover 36 by interfacing spacers 86. These sensors respond to the magnetic field of magnet 83 and provide an electrical signal which reports to the electronics within the console the position of the transducer as it moves back and forth along the lead screw.

Beginning in the position shown in solid line form in FIG. 3, magnet 83 is centered and directly in line and below sensor 84. In this position the centerline of transducer 80, which corresponds to the geometric center of focus of the transducer, is at its extreme end of travel in one direction along the path and signifies the starting position for one frame of imaging information. That first frame is completed when the pawl, holder and transducer move to the position identified in phantom line form directly beneath Hall effect sensor 85. This position denotes the end of travel in that first direction and the beginning point for the reverse direction of travel across the same path and over the same axis of drive screw 75. This position also signifies the end of one frame of image information and the start of a second frame. The transducer then moves again to the left returning to its starting position and thus ending the second frame of image information.

Based upon the RPM's of drive motor 61, the pitch of level winding drive screw 75 and the centerline distance between Hall effect sensors 84 and 85, the disclosed system generates three trips of the transducer and thus three frames of image information each second. This is approximately one-fifth of the rate for real-time imaging which is generally regarded as beginning at approximately 15 frames per second. However, since the disclosed probe is intended for imaging and diagnosis of principally stationary masses, real-time imaging with this specific structural arrangement is not required. However, it should be understood that by increasing the drive speed of the motor, possibly incorporating a larger motor, and with counterbalancing to reduce vibration, real-time imaging can be achieved while still encompassing the scanning design of the present probe (see FIG. 7). Another option to achieve real-time imaging is to provide a number of lightweight transducers in a linear series and uniformly move the series back and forth over a shorter distance in each direction which is roughly equal to the radius of the transducer element (see FIG. 6). The distance of travel for a full frame using n transducers is 1/n of the distance for a single transducer.

In order to aid the smoothness and accuracy of travel of the pawl holder and transducer back and forth across drive screw 75, a parallel guide shaft 89 is securely anchored (see FIG. 9) at one end in plug 56 and at the opposite end in top cover 36. As is best illustrated in FIG. 5, holder 78 is configured with an open channel 90 which receives guide shaft 89.

In the design and utilization of water-filled enclosures for ultrasonic imaging, it is important that the fluid-filled cavity be free of any air bubbles or voids. It is als important to be able to drain the fluid, typically distilled water, for repair or servicing of the internal components within the probe. In order to facilitate both objectives, the upper end corner of enclosure 34 is provided with a filling hole which is closed by plug screw 91. The placement of the hole in the corner enhances the ability to fill the entirety of the cavity without any air bubbles. A fill port or hole placed along a substantially flat wall may enable trapped air due to surface variations and irregularities.

In the preferred embodiment, transducer 80 is attached to holder 78 by means of an adhesive compound. Further, various relief and channels are provided as part of holder 78 so that the necessary electrical connections and wire routings can be achieved. The wires at their point of attachment are encapsulated or potted and routed to cable 22 for communication with console 21.

Another feature of the present invention is the tapered nature of wall portion 37 which permits a more compact and lightweight design. By arranging the transducer drive mechanism so as to create a linear scan, a single path of travel is involved and the size of the focused ultrasound beam as it passes through the membrane covering 38 over the open window can be precisely controlled. The width of the window opening (the lower portion of FIG. 5) is sized to its minimum requirements. Some slight tapering of wall portion 37 is permitted in the other direction again for the reason that the focused beam of ultrasound will be narrower than the diameter of the generating transducer 80. Although upper clearance must be left for the edge of the transducer as it moves back and forth, the exit opening (window) must only be sized for the edge-to-edge travel of the ultrasound beam which is present at that exiting location.

This particular tapering head design, the incorporation of a small, lightweight self-focusing transducer and a linear drive configuration for scanning all contribute to a unique, practical and highly efficient scanning probe which is lightweight though durable and reliable.

Figure 6:
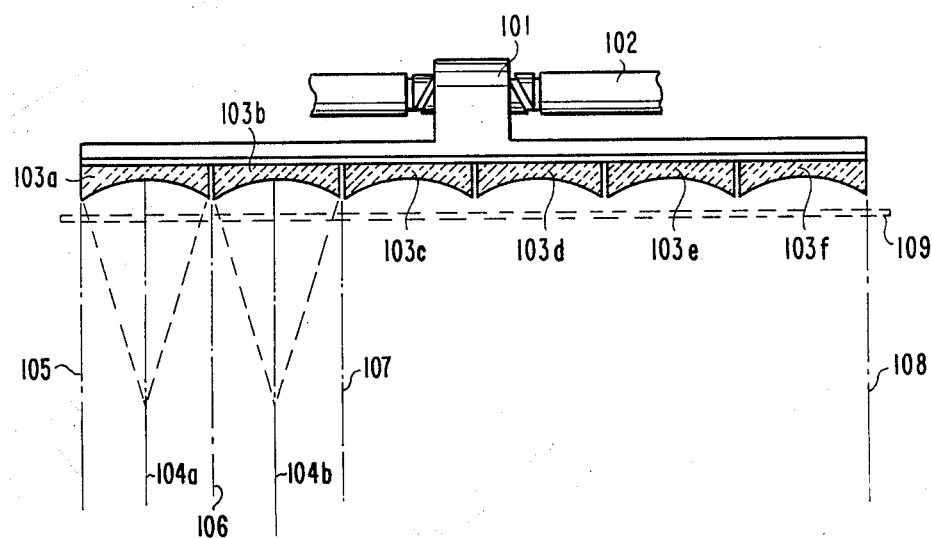
FIG. 6 is a partial, diagrammatic side elevation view of an alternate embodiment of the present invention.
Figure 7:
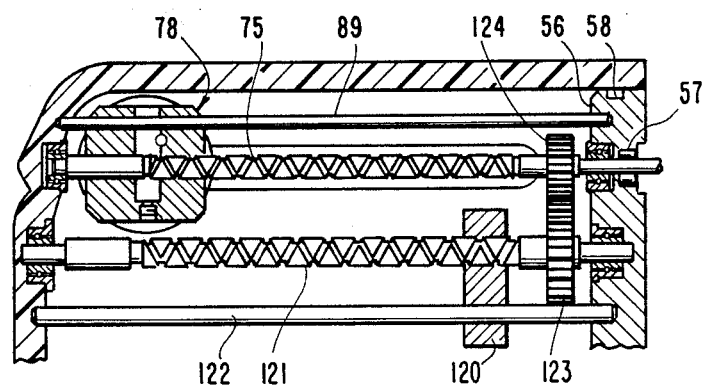
FIG. 7 is a partial, diagrammatic top plan view of an alternate embodiment of the present invention.

Referring to FIG. 6, there is illustrated in partial and diagrammatic form an alternate embodiment of the present invention which may be employed for real-time imaging applications. The changes to probe 20 which are represented by the FIG. 6 embodiment include the distance of travel by holder 102 along modified level wind drive screw 102 and the number of lightweight transducers which are attached to holder 101 in series and side by side as represented by reference numerals 103(a)–103(f). Holder 101 is attached to and in common with all six transducers and is illustrated in a center position. The distance of travel which is possible from this center position in either a left or right direction is equal and is equal to the radius of each transducer 103(a)–103(f). The level wind drive screw is modified so that each full frame of travel in any one direction before reversing direction (unidirectional drive motor) is equal to the diameter of each transducer.

Due to these dimensional relationships, rotation of the drive motor shaft results in travel of holder 101 and correspondingly of each transducer from this centerline position illustrated to either the left or right a distance equal to the radius of any one transducer of the adjacent series. For example, with leftward movement centerline 104a which corresponds to the focus axis of transducer 103a will be moved to edgeline 105 while the centerline (focus axis) 104b of transducer 103b travels to line 106. As holder 101 reverses direction and makes a full sweep to the right, each transducer moves to the right a distance equal to its diameter. Centerline 104a travels from edgeline 105 to line 106 while centerline 104b travels from line 106 to line 107. As should be understood, each transducer is sized virtually the same and each moves in a virtually identical fashion the same distance to either the left or right depending on the direction of travel of holder 101.

The six transducers which are arranged in series create a full linear scan (one frame) from line 105 to line 108, even though any one of the transducers moves only one sixth of that full scan distance. The simultaneous image-representative signals received by each transducer and which correspond to one-sixth of the scan width (a single frame) are able to be displayed as a single frame image due to scan conversion circuitry.

For use with the FIG. 6 embodiment, motor 61 operates at the same speed (RPM) with the six transducers as it operated with a single transducer in the earlier embodiment. Level wind drive screw 102 has the same pitch as drive screw 75 but is simply shorter such that it reverses direction of the holder in one-sixth the distance traveled for the single transducer holder. Combining this information with the fact that in the earlier described embodiment, the holder and single transducer moved at a rate of three frames per second, the resultant rate for the six transducer arrangement is 18 frames per second, which is a "real-time" frame rate.

A further variation with the FIG. 6 embodiment is the placement of rigid window 109 in close proximity to the transducer elements. The significance of this structural change is that the focal depth of each transducer is positioned deeper into the body, assuming the same acoustical and focusing characteristics for transducers 103a–103f as were present transducer 80. It is to be understood that by varying the size of wall portion (stand-off) 37 or by changing the focusing characteristics of the transducer(s), the depth of focus into the body can be changed. Focal depth (depth at which the focused spot exists) can also be changed by dynamic focusing or by multiple zone focusing, such as near, mid- and far-field focus zones. Dynamic focusing is achievable by an electronically phased annular array for the transducer(s) of the system. In multiple zone focusing, the full dynamic zone range is divided up into discrete zones. This approach represents a compromise between fixed focus and dynamic focus.

An alternative to multiple transducers in order to obtain a real-time frame time is to simply increase the RPM speed of the motor. If the motor speed of the FIG. 3 embodiment is increased by five times, the frame rate goes from these frames per second to fifteen frames per second. This fifteen frames per second rate is regarded as being "real-time." One concern with simply increasing the motor speed in order to achieve this higher RPM rate is that vibration becomes a factor and the ease of handling and stability of the probe is adversely affected. In order to preclude vibration and related handling problems, counterweighting or balancing needs to be provided. Referring to FIG. 7, one counterbalancing approach is illustrated in partial, diagrammatic form.

In order to better understand FIG. 7, consider the FIG. 4 illustration and envision motor 61 driving the holder and transducer back and forth at the higher rate of fifteen frames per second. This five times speed increase creates vibration and a handling instability in the probe. By providing a virtual duplication of the drive screw and holder mass in a side-by-side arrangement and in a reversed or opposite fashion, this added structure is suitable to offset the vibration forces generated by the rapid rate of movement of the holder and single transducer. This offset and counterweighted balance provides probe stability and reduces vibration so that high motor speeds can be utilized.

More specifically, and in reference to FIG. 7, a counterbalance mass 120 is provided and is pawl-driven on level wind drive screw 121. This particular mass 120 although physically smaller than the holder and transducer combination, has the identical weight to the transducer and holder assembly and a similar center of gravity relative to its placement on the level wind drive screw 121. Stabilizing shaft 122 is also employed, again in a manner similar to that of stabilizing bar 89 which is used in combination with the holder and transducer. Although motor 61 is not changed in this particular application, except as its speed of rotation, the output of the motor which is in a direct drive relationship to level wind drive screw 75 also drives drive screw 121 by means of a gearing arrangement consisting of driven gear 123 and driving gear 124. Driven gear 123 is rigidly secured to the shaft portion of drive screw 121 which is bearingly mounted at each end. Gears 123 and 124 are identical. As the holder and transducer moves back and forth at a rapid rate of travel, counterbalancing mass 120 correspondingly moves though in an offsetting or opposite direction. This matched, though opposite, travel creates a counterweighting or counterbalancing to the transducer and holder that eliminates the undesirable level of vibration caused by the increased motor speed.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A portable, hand-held, ultrasonic scanning probe for use with energizing and receiving means for imaging sections of a body by transmitting ultrasonic energy into the body and receiving image-representative signals from the body, comprising:
   a fluid-tight enclosure;
   fluid contained within said enclosure;
   transducer means disposed within said enclosure and operable in response to said energizing and receiving means to generate an ultrasound beam into the body and receive image-representative signals back; and
   linear drive means for moving said transducer means back and forth on a common axis in a linear path, said linear drive means including a level wind drive screw and a cooperating holder, said transducer means being secured to the said holder, said holder remaining static relative to said transducer means.

2. The scanning probe of claim 1 which further includes a one-directional, rotary drive motor coupled to said level wind drive screw.

3. The scanning probe of claim 2 which further includes magnetic field sensors, one at each end of said path, and a cooperating magnet carried by said holder.

4. The scanning probe of claim 3 wherein said transducer means includes a transducer of a plano-concave, focusing configuration.

5. The scanning probe of claim 4 wherein said fluid-tight enclosure includes a tapered portion through which said ultrasonic energy and received signals pass.

6. An apparatus for imaging sections of a body, comprising:
   energizing and receiving circuitry means for generating and receiving electrical signals;
   data presentation means electrically coupled to said energizing and receiving circuitry means for receiving data and presenting it in a preciptible form; and
   a portable, hand-held, scanning probe electrically coupled to said energizing and receiving circuitry means and comprising:
   a fluid-tight enclosure;
   fluid contained within said enclosure;
   transducer means disposed within said enclosure and operable in response to said energizing and receiving circuitry means to generate an ultrasound beam into the body and receive image-representative signals back; and
   linear drive means for moving said transducer means back and forth on a common axis in a linear path, said linear drive means including a level wind drive screw and a cooperating holder, said transducer means being secured to said holder, said holder remaining static relative to said transducer means.

7. The apparatus of claim 6 which further includes a one-directional, rotary drive motor coupled to said level wind drive screw.

8. The apparatus of claim 7 which further includes magnetic field sensors, one at each end of said path, and a cooperating magnet carried by said holder.

9. The apparatus of claim 8 wherein said transducer means includes a transducer of a plano-concave, focusing configuration.

10. A portable, hand-held, ultrasonic imaging probe for use in transmitting ultrasound into a body and receiving ultrasound echoes back from the body, comprising:
    a transducer suitably arranged with drive circuitry to generate an ultrasound beam and convert received echoes into image-representative electrical signals; and
    linear drive means for moving said transducer back and forth in a linear path, said linear drive means including a DC motor coupled to a level wind drive screw.

11. A portable ultrasonic scanning probe for use with energizing and receiving means for imaging sections of a body by transmitting ultrasonic energy into the body and receiving image-representative signals from the body, comprising:
    a fluid-tight enclosure;
    fluid contained within said enclosure;
    transducer means disposed within said enclosure and operable in response to said energizing and receiving means to generate an ultrasound beam into the body and receive image-representative signals back;
    drive means for moving said transducer means back and forth on a common axis in a linear path, said drive means including a level wind drive screw and a cooperating holder, said transducer means being secured to said holder, said drive means further including a one-directional, rotary drive motor coupled to said level wind drive screw; and
    a pair of oppositely disposed magnetic field sensors, one of each end of said linear path, which remain stationary relative to the movement of said transducer and a cooperating trigger carried by said holder so as to define the edges of each frame of image data.

12. An ultrasonic imaging probe for use in transmitting ultrasound into a body and receiving ultrasound echoes back from the body, comprising:
    a transducer suitably arranged with drive circuitry to generate an ultrasound beam and convert received echoes into image-representative electrical signals; and
    drive means for moving said transducer back and forth in a linear path, said drive means including a unidirectional motor coupled to a level wind drive screw.

* * * * *